United States Patent
Larson et al.

(10) Patent No.: US 7,153,411 B2
(45) Date of Patent: Dec. 26, 2006

(54) METHOD FOR CLEANING AND POLISHING METALLIC ALLOYS AND ARTICLES CLEANED OR POLISHED THEREBY

(75) Inventors: Steve Larson, Lino Lakes, MN (US); Daniel VanCamp, Covington, WA (US); Nielsen Eric, Redmond, WA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 213 days.

(21) Appl. No.: 10/748,493

(22) Filed: Dec. 30, 2003

(65) Prior Publication Data
US 2005/0145508 A1    Jul. 7, 2005

(51) Int. Cl.
C25F 3/22    (2006.01)
C25F 3/24    (2006.01)
C25F 3/26    (2006.01)
C25F 1/00    (2006.01)

(52) U.S. Cl. ............... 205/661; 205/640; 205/710
(58) Field of Classification Search ............. 205/684, 205/640, 661, 710
See application file for complete search history.

(56) References Cited

U.S. PATENT DOCUMENTS

| | | | | |
|---|---|---|---|---|
| 2,334,698 A | * | 11/1943 | Faust | 428/687 |
| 2,840,468 A | | 6/1958 | Brenner et al. | 420/512 |
| 3,647,654 A | | 3/1972 | Toledo et al. | 204/140.5 |
| 4,148,670 A | * | 4/1979 | Kelly | 148/247 |
| 4,663,005 A | * | 5/1987 | Edson | 205/676 |
| 4,686,017 A | | 8/1987 | Young | 205/234 |
| 5,344,425 A | | 9/1994 | Sawyer | 606/198 |
| 5,421,955 A | | 6/1995 | Lau et al. | 216/48 |
| 5,560,814 A | | 10/1996 | Burkhart et al. | 205/271 |
| 5,746,691 A | | 5/1998 | Frantzen | 600/36 |
| 5,891,507 A | | 4/1999 | Jayaraman | 427/2.25 |
| 5,997,703 A | | 12/1999 | Richter | 204/297 |
| 6,086,455 A | | 7/2000 | Frantzen | 451/36 |
| 6,183,353 B1 | | 2/2001 | Frantzen | 451/104 |
| 6,254,631 B1 | | 7/2001 | Thompson | 623/1.15 |
| 6,254,632 B1 | * | 7/2001 | Wu et al. | 623/1.15 |
| 6,299,755 B1 | | 10/2001 | Richter | 205/651 |
| 6,344,055 B1 | | 2/2002 | Shukov | 623/1.15 |
| 6,355,058 B1 | * | 3/2002 | Pacetti et al. | 623/1.15 |
| 6,361,637 B1 | | 3/2002 | Martin et al. | 156/187 |
| 6,375,826 B1 | | 4/2002 | Wang et al. | 205/684 |
| 6,416,650 B1 | | 7/2002 | Ho | 205/640 |
| 6,527,938 B1 | | 3/2003 | Bales et al. | 205/229 |
| 6,537,202 B1 | | 3/2003 | Frantzen | 600/36 |
| 6,558,231 B1 | * | 5/2003 | Taylor | 451/36 |
| 6,568,432 B1 | | 5/2003 | Matsutani et al. | 140/71 R |

(Continued)

FOREIGN PATENT DOCUMENTS

DE    25 40 652    3/1977

(Continued)

Primary Examiner—Roy King
Assistant Examiner—Michael P. Alexander
(74) Attorney, Agent, or Firm—Vidas, Arrett & Steinkraus, P.A.

(57) ABSTRACT

A method of cleaning and polishing an alloy comprising at least one noble metal and at least one non-noble metal, the method including the steps of submerging said alloy in an electrolytic acidic bath comprising at least one chelating or complexing agent including sulfur, and applying a multiple pulse periodic reverse waveform, and articles cleaned and/or polished thereby.

11 Claims, 4 Drawing Sheets

U.S. PATENT DOCUMENTS

| | | | |
|---|---|---|---|
| 6,599,415 B1 | 7/2003 | Ku et al. | 205/670 |
| 6,605,539 B1 | 8/2003 | Lee et al. | 438/693 |
| 6,663,765 B1 | 12/2003 | Cherkos | 205/668 |
| 6,676,989 B1 | 1/2004 | Kirkpatrick et al. | 427/2.28 |
| 6,679,980 B1* | 1/2004 | Andreacchi | 204/272 |
| 2002/0038767 A1 | 4/2002 | Trozera | 205/667 |
| 2002/0130049 A1* | 9/2002 | Chen et al. | 205/640 |
| 2002/0198589 A1* | 12/2002 | Leong | 623/1.15 |
| 2003/0018380 A1 | 1/2003 | Craig et al. | 623/1.15 |
| 2005/0089438 A1* | 4/2005 | Stinson | 420/466 |
| 2005/0121390 A1* | 6/2005 | Wallace et al. | 210/638 |

FOREIGN PATENT DOCUMENTS

| | | |
|---|---|---|
| DE | 29914243 U1 * | 1/2001 |
| JP | 50 001351 | 1/1975 |
| JP | 60 077999 | 5/1985 |
| JP | 408302500 A * | 5/1995 |
| JP | 08 302500 | 11/1996 |
| RU | 2 184 801 | 7/2002 |
| SU | 802412 B * | 2/1981 |
| SU | 1440636 A1 * | 11/1988 |
| WO | 02/078764 | 10/2002 |

* cited by examiner

US 7,153,411 B2

1

METHOD FOR CLEANING AND POLISHING METALLIC ALLOYS AND ARTICLES CLEANED OR POLISHED THEREBY

FIELD OF THE INVENTION

The present invention relates to the field of descaling and electropolishing of metals, particularly alloys composed of dissimilar metals and to methods and apparatuses used therefore. The present invention is particularly useful for descaling and electropolishing of medical devices, particularly stents.

BACKGROUND OF THE INVENTION

Stents are used in conjunction with a medical procedure known as balloon angioplasty to restore blood flow through obstructed or partially obstructed arteries. In an angioplasty procedure, a balloon catheter is inserted into an artery through a small incision and is advanced to the site of an arterial lesion via a catheter. Subsequently, the balloon catheter is inflated to compress the accumulated atherosclerotic plaque against the artery wall, thereby restoring blood flow through the vessel. In some cases, the expanded artery will collapse after deflation of the balloon catheter or will slowly narrow over time, a process referred to in the art as restenosis.

Stents are small, tubular structures which are implanted in the vessel to provide mechanical support to the arterial wall. The use of stents has been shown to result in a lower incidence of restenosis which has consequently lead to a more widespread use of stents in the treatment of vascular disease.

Stents are fabricated from a variety of metals, among other types of materials, including, for example stainless steel, most commonly 316L stainless steel, and nickel-titanium alloys such as NITINOL. Stent materials are selected based on mechanical properties, corrosion resistance and vascular compatibility.

Typically, the stent manufacturing involves machining a specially designed stent pattern into thin walled tubes or flat sheets of the desired metal. This cutting is preformed utilizing laser beam machining (LBM), electrode discharge machining (EDM) or chemical dissolution ("chemical milling"). In the case of flat sheets, the machined part is then rolled and welded into a tubular shape.

The LBM technique cuts the material with a focused, high-energy beam of light. The EDM technique utilizes an electrical spark discharge to cut in a similar manner. The chemical milling technique consists of masking the metal with a chemically resistant material and then dissolving away the exposed metal with a chemical solution. The masking is then removed resulting in the machined stent.

In both the LBM and EDM techniques localized heating of the machined part occurs, resulting in melted and oxidized metal byproducts along the cut surfaces. Additionally, all three machining techniques result in a coarse, rough surface and sharp edges. Many processes have been developed to remove the byproducts created by the machining operations ("descaling" or "cleaning"). A separate process is used to polish the stent surface and round sharp edges ("electropolishing").

Descaling methods are known in the art for many metals. One example is immersion of stainless steel or nitinol alloys in a heated mixture of hydrofluoric acid and nitric acid. Another example is the electrolytic treatment of stainless steel in a sulfuric acid solution. In these operations, the machining byproducts are removed leaving behind a clean part that is free of remnant debris from the cutting operation. Alternately mechanical grit blasting is sometimes used to remove oxides from titanium alloys. Other procedures for descaling are well known to those skilled in the art.

The principles of electropolishing, particularly with regard to stainless steel alloys, are also known in the art. Electropolishing typically involves dissolving and smoothing the metal surface by electrolysis. Using this method, an item to be electropolished is immersed in an electrolyte which typically comprises a conductive, acidic solution. A counter electrode is also immersed in the solution and is typically connected to the negative terminal of the power supply (creating a cathode). Typically, the positive terminal of the power supply is attached to the part, thereby completing the electric circuit. An appropriate electrical potential is applied between the workpiece and the cathode and current flows.

Upon the passage of electric current through the electrolyte, metal is dissolved from the anode surface creating a resistive film on the surface of the workpiece. Protrusions on the anode surface dissolved faster than depressions producing a smoother surface. Examples of electropolishing processes include: dissolution of stainless steel in phosphoric acid and sulfuric acid; dissolution of titanium (or alloys) in perchloric acid and methanol, and dissolution of stainless steel in glycerol and sulfuric acid. Additionally, gold can be electropolished through dissolution in a solution comprised of potassium cyanide, potassium tartrate, potassium ferrocyanide, disodium hydrogen phosphate, and ammonia hydroxide.

The now polished item is typically immersed in nitric acid. The nitric acid is effective in removing certain metallic oxides, salts or other impurities such as mixed iron or other reactive oxides or particulates. The goal is to ensure high Cr/Fe ratios and homogenous surface chemistry free of residual metal compounds formed during the electropolishing operation that may compromise the surface with respect to biocompatibility. The result is a clean, biocompatible, corrosion resistant surface.

Many metal medical implants contain active transition metals, which form passive oxide surfaces. The stable metal oxide is resistant to corrosion. Processes for descaling and electropolishing these alloys are known in the art.

More recently, however, other properties such as the radiopacity of the material, i.e. the x-ray absorption properties, has become a consideration in order to observe the stent during both the medical procedure and during follow up exams using fluoroscopy to visualize it. Consequently, new metal alloys have emerged in order to improve the radiopacity of the stent. Examples of such alloys include, for example, those of cobalt, chrome, and tungsten such as L-605, for example.

Yet another way in which the radiopacity may be improved is to add a noble metal to an existing alloy, such as the addition of platinum to 316L stainless steel such as that found in conunonly assigned copending U.S. patent application Ser. No. 10/112,391, the entire content of which is incorporated by reference herein.

This approach has resulted in a marked improvement in the fluoroscopic visualization of stents. However, the addition of noble metals to the stent material complicates the manufacturing process due to the chemical inertness of noble metals. Thus, currently employed descaling and polishing operations are neither efficacious nor effective for uniformly dissolving alloys having noble metals. Consequently, there remains a need in the art for an improved method for descaling and electropolishing alloys having noble metals as part of the alloy composition.

SUMMARY OF THE INVENTION

In a broad sense, the present invention relates to a method of descaling and electropolishing metals, particularly alloys composed of dissimilar metals such as those composed of both noble and active transition metals.

The present invention finds particular utility for descaling and electropolishing medical devices such as stents which are composed of both noble and active transition metals.

In one aspect, the present invention relates to cleaning and/or electropolishing stents which are formed from noble metal enriched alloys, particularly platinum group metals alloyed with active transition metals and more particularly platinum-enriched stainless steel alloys. Examples of other metals which may be employed in the present invention include, for example, platinum, palladium, rhodium, iridium, ruthenium, rhenium, gold, silver, copper, osmium, and so forth may be employed as well as long as the metal mixtures have differential chemical activity compared to the conventional process chemicals employed. While there may be some dispute as to which metals may be included in the noble metal category, for purposes of this invention, such metals will be referred to hereinafter as noble metals or platinum groups metals (PGM's).

The addition of noble metals to existing alloys has been found to provide enhanced radiopacity without negatively impacting the mechanical properties of the metal.

The present invention provides enhanced chemical processing of a variety of active transition metals, and alloys containing active transition metals which are enriched with at least one noble metal(s). Examples of useful metals include, for example, stainless steel, cobalt-chrome alloys, nickel-titanium alloys such as NITINOL, and other metals having chrome, niobium, tantalum, hafnium, titanium, molybdenum, tungsten, zirconium, and so forth, and alloys thereof.

The cleaning or electropolishing steps may be incorporated into any stent manufacturing process. A typical process includes the steps of providing a tubular member, cutting a stent pattern in the tubular member, cleaning the tubular member, polishing the tubular member, passivating the surface of the tubular member, and rinsing and drying the now formed stent.

The process of making the stent may incorporate any combination of the above steps in any order. Furthermore, rinsing may be conducted between each cleaning and/or polishing steps, and there may be multiple cleaning and/or polishing steps as well. Alternatively, the stent may be formed from a flat sheet stock which is then rolled and welded into the tubular shape.

The present invention also relates to an acidic composition for use in an electrochemical cleaning or polishing process including phosphoric acid, hydrochloric acid, a halide salt, and a complexing agent having at least one sulfur atom which is available for chemical bonding. Examples of suitable complexing agents include, but are not limited to, thiourea ($CH_4N_2S$) or derivatives of thiourea, thiouronium salts, thiocarboxylic acids or salts thereof, and so forth. Such compositions find utility for electropolishing or descaling noble metal enriched alloys.

Fluoride salts, hydrofluoric acid, or other fluoride containing compounds may be required to disrupt more stable metal oxides such as those of titanium, niobium, tantlum, zirconium, hafnium, for example, and so on and so forth.

Suitably, a cyclic current or voltage waveform is applied to the metal part. In some embodiments, the waveform is a pulsed, alternating polarity waveform.

In other embodiments, a sine wave, square wave or pulse train in any shape or combination of no polarity or alternating polarity of the waveform is employed.

A "rest" period of zero or near zero voltage or zero or near zero current may also be included in the current/voltage waveform to balance the polishing film diffusion requirements. The response current or voltage during the "rest" period may or may not be limited, either in constant current or in constant voltage mode, to allow charge dissipation of the part during the "rest".

In some embodiments, the electrolyte solution is employed for use in cleaning or electropolishing stents formed from platinum enriched stainless steel alloys.

Other features and advantages of the present invention will become apparent from the following detailed description.

DETAILED DESCRIPTIONS OF THE PREFERRED EMBODIMENTS

Figure 1:
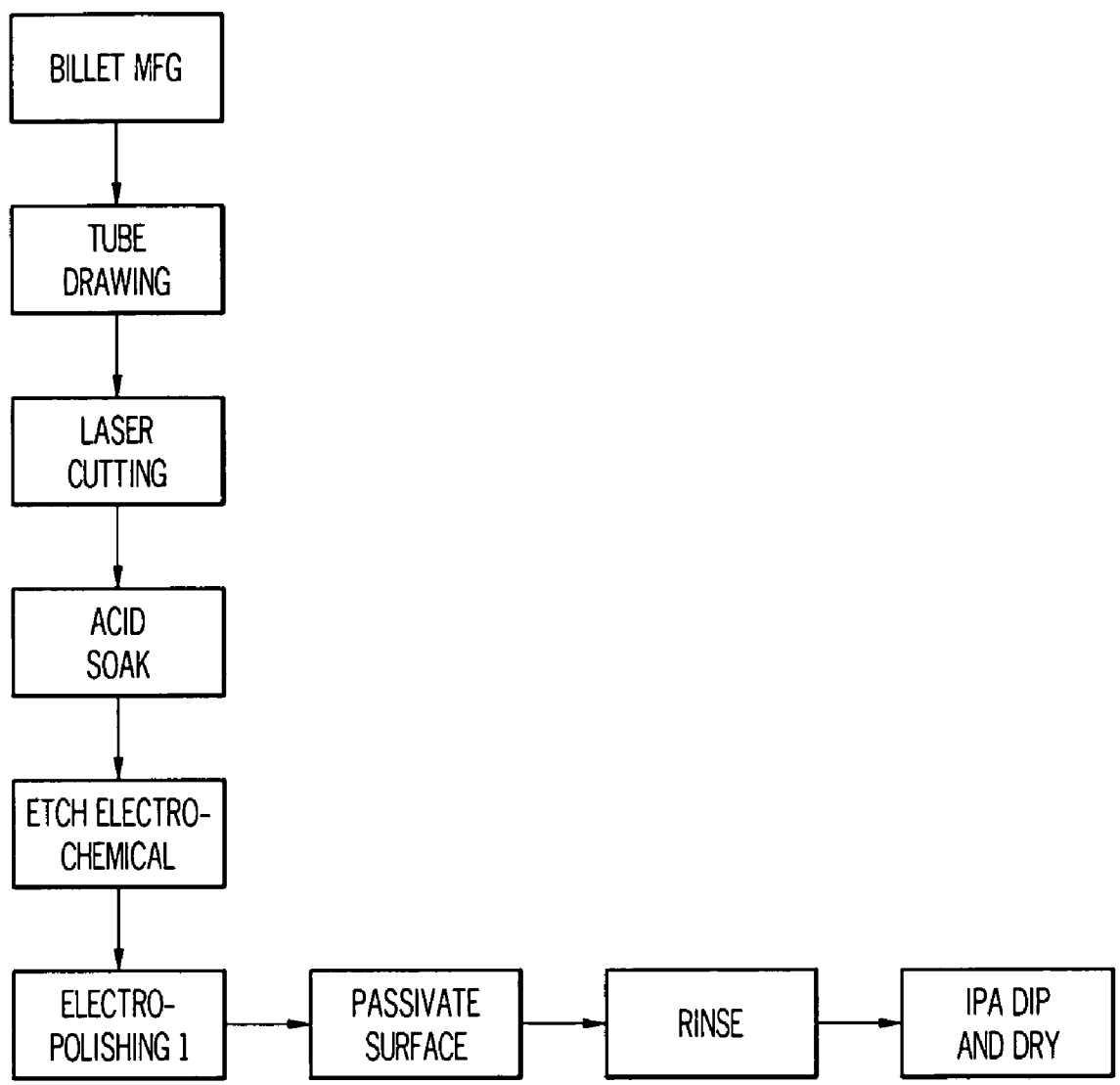
FIG. 1 is a flow diagram illustrating a stent manufacturing process according to the present invention.

While this invention may be embodied in many different forms, there are described in detail herein specific embodiments of the invention. This description is an exemplification of the principles of the invention and is not intended to limit the invention to the particular embodiments illustrated.

The cleaning or electropolishing process according to the present invention finds particular utility for cleaning or electropolishing those alloys having both noble and active transition metals. The method can be effectively used at room temperature and requires little or no agitation thus offering advantages over other currently used processes for polishing stainless steel or similar alloys. While it is recognized that agitation may be efficacious in certain geometric configurations from a cleanliness standpoint, the complexity of stent surface geometries makes it very difficult to provide the exact same surface solution flow dynamics on all surfaces. In this respect, agitation may or may not be efficacious depending on the nature of surface geometries and the governing conditions of the bath.

The process according to the present invention is particularly useful for medical devices formed from alloys having both noble and active transition metals. These alloys offer advantages over other alloys including, for example, enhanced radiopacity, mechanical properties equivalent to those of high-grade steel, catalytic surfaces, low surface resistance and enhanced resistance to oxidative environments.

In some embodiments, the article is a stent formed from a noble-metal enriched stainless steel alloy. Stents are generally tubular expandable structures which expand from a first position, wherein the stent is sized for intravascular insertion, to a second position, wherein at least a portion of the exterior surface of the stent contacts the vessel wall. The expanding of the stent is accommodated by flexing and bending of the interconnected struts through the generally tubular structure.

The stent according to the present invention may be manufactured from a noble metal-enriched alloy. In one particular embodiment, the stent is manufactured of an alloy of stainless steel alloy such as 316L stainless steel alloy, and platinum (e.g. 316L is diluted with mostly platinum). Such a stent can be manufactured having wall thicknesses of less than about 0.005 inches while maintaining sufficient radiopacity to be radiopaque during and after placement in the body lumen. The stents manufactured from such alloys exhibit enhanced radiopacity and corrosion resistance while maintaining mechanical and structural properties similar to stainless steel alloys.

The stents may be manufactured having from about 2 wt-% to about 70 wt-% of the noble metal, more suitably about 5 wt-% to about 50 wt-% of the noble metal, and most suitably about 12 wt-% to about 30 wt-% of the noble metal.

In one embodiment, the alloy includes stainless steel, platinum, chromium and nickel. The chromium is present from about 10 wt-% to about 20 wt-% and the nickel is present from about 5 wt-% to about 15 wt-%. The alloy further may include from about 10 to about 40 wt-% iron.

In one embodiment, the alloy includes about 39 wt-% iron, about 30 wt-% platinum, about 18 wt-% chrome, about 9 wt-% nickel, about 3 wt-% molybdenum and about 1 wt-% manganese.

The present invention also finds utility in the cleaning or polishing of alloys such as those described in U.S. Pat. No. 2,840,468, "Novel Gold Alloys and Potentiometer Wires Produced From Them," the entire content of which is incorporated by reference herein. The alloys described therein are available from Sigmund Cohn Corporation under the trandename of LTC®.

The present invention also finds utility for cleaning and polishing alloys such as 94 Pt-6W also available from Sigmund Cohn Corporation.

The present invention also finds utility in the cleaning or polishing of alloys such as those described in commonly assigned, copending U.S. patent application Ser. No. 10/112,391, the entire content of which is incorporated by reference herein.

The stents of the present invention are formed by a process which includes the steps of providing a tubular member, cutting a stent pattern in the tubular member, acid soaking or descaling the tubular member, electrolytic cleaning of the tubular member, polishing the tubular member, passivating the surface of the tubular member and rinsing and drying the tubular member, but not necessarily in that order.

This is intended as a general guide for the steps involved in forming the stents according to the present invention. The process may include these steps in any combination, and some steps may not necessarily be required. Those skilled in the art will recognize the utility of the process as described and claimed herein in the chemical milling of medical devices such as stents. However, it is not intended that the present invention be limited to medical devices, but may find utility for polishing or cleaning any article formed from alloys having both noble and active transition metals.

Furthermore, there may be multiple cleaning or polishing steps involved in the process, and rinsing may be conducted after each cleaning or polishing step.

FIG. 1 is a flow diagram illustrating a general stent manufacturing process. A platinum-enriched stainless steel stent will be used for purposes of illustration.

The process of manufacturing a stent begins with a billet or preform as shown in the first box in FIG. 1.

The second step of the process is tube drawing. Tube drawing is a reduction process in which one end of a tube is grasped and pulled through a die that is smaller than the tube diameter to reduce the diameter. To obtain the desired size, a series of successive reductions, or passes, may be conducted. In addition, annealing steps may be conducted to obtain the desired mechanical properties, grain size and attendant corrosion resistance.

Once the tube has been drawn, the stent pattern may be cut into the noble metal-enriched alloy. Methods of cutting such stent patterns are known to those of skill in the art and include, laser beam machining, electrode-discharge machining and chemical milling. However, any method known to those of skill in the art may be employed.

If a laser is employed, the type of laser will in part depend on the substrate material from which the stent is formed. For example, when the stent substrate is metal, such as stainless steel or NITINOL, an Nd:YAG laser, $CO_2$ laser, frequency doubled YAG laser, diode laser, and so forth may be used.

The third box shown in FIG. 1 represents the tube cutting process during which, stent patterns may be cut into a thin walled metal tube, commonly referred to in the art as a "hypotube". Typically, laser cutting is performed using an assist gas, such as oxygen, nitrogen, argon or other inert or inactive gases. In some embodiments of the present invention, it has been found advantageous to employ 100% oxygen as the assist gas depending on the approach being made to in the post LBM to remove the cutting debris.

This laser cutting operation produces a plasma that removes a predetermined section of the tube to form the stent pattern. The material which is removed is either vaporized or melted in the oxygen rich environment under high gas flow conditions. Hence new phases and derivative compositions of the alloy material are observed on the cut face and inner diameter of the stent. Since the melted metal on the cut face cools at different rates depending on depth and other factors, there is a tendency for the metal to segregate into noble metal rich and noble metal poor phases. The oxygen exposure at high temperature promotes the formation of metal oxides in that material. The remelted material and oxides formed during the cutting process are collectively known as "dross". For example, the dross may contain carbon sourced from a cutting fluid (if utilized in the process), transition metal(s), transition metal mixed oxides, noble metal(s), noble metal mixed oxides, and mixtures thereof.

In the case of platinum-enriched stainless steel, the dross is composed mainly of carbon, platinum, chrome, oxygen and iron. The dross forms a film on the cut edge of the strut and nodular formation on the inner diameter strut face. Additionally, spherical particles composed primarily of platinum, iron and nickel are intermixed with the inner diameter dross. Often, a thin layer of platinum is found under the cut face dross depending on laser parameters employed.

The active transition metals such as chrome, iron and nickel, for example, readily form oxides and dissolve in acid baths when electric current or voltage is applied. The noble metals, however, do not readily form oxides nor do they readily react or dissolve in conventional acid baths when current is applied.

In the fourth box of the process represented by FIG. 1 includes a post laser cleaning step in which the stent is submersed in an acid bath is depicted. The acid bath is typically composed of strong organic or inorganic acids, or mixtures thereof. Examples of such acids include, but are not limited to, hydrofluoric acid or a derivative thereof, tetrafluoroboric acid, nitric acid, hydrochloric acid, sulfuric acid, phosphoric acid, or mixtures thereof. Depending on the acids used, this soak can facilitate solubilization of the metal/metal oxides formed which improves dross removal.

Note that dross particles are composed of significantly higher surface area relative to the workpiece and as such, react faster than normal passive surface oxides that are present on the substrate. This is one mechanism that allows efficient removal of dross particles with little dissolution of the workpiece. Thus, high surface area dross may be designed into the cutting operations. Additionally, the cutting operations may be designed to provide "chemical selectivity" to the dross. In this respect, any chemical operation used to remove iron, nickel, chrome, molybdenum and mixed metals and oxides thereof, may be used with respect to efficiently concentrating and leaving behind all the unreacted platinum that was an integral part of those mixtures. This platinum is now available for a specific targeted reaction to remove it without risk of dissolving a significant quantity of the workpiece. In this respect, the integrated process framework can improve the effectiveness of the electrolytic cleaning step(s) as described below.

An acid soak including about 0.1 M to about 5 M tetrafluroboric acid and about 2 M to about 5 M nitric acid at a temperature of about room temperature to about 90° C. has been found to be effective. The time interval required depends on the temperature and the acid concentrations employed. Even more suitably, an acid soak solution of about 1 M to 1.5 M tetrafluroboric acid and about 3 M to about 3.7 M nitric acid at temperature of about 70° C. for 30 minutes has been found to be effective for use herein.

Electrolytic steps can be used to achieve superior cleaning with less substrate mass removal. An effective electrolytic cleaning solution includes conductivity, complexing agents for each material to be dissolved, and a waveform capable of generating the desired reactions to selectively solubilize specific dross compositions, without dissolution of the base metal (e.g. stent). Such steps may be added in addition to other cleaning steps, or as an alternative to other cleaning steps.

The present invention has found that by employing a multiple pulse waveform in combination with a complexing agent according to the invention, efficacious descaling and electropolishing of alloys made of noble and active transition metals can be achieved.

Suitably, the complexing agent has at least one sulfur atom available for covalent bonding. The complexing agent may, however, include carbon, nitrogen, phosphorous, arsenic, chlorine, bromine, and so forth.

Historically, cyanide compounds have been utilized for complexing noble metals. However, while cyanide is an effective complexing agent, it has the disadvantage of generating highly toxic hydrogen cyanide gas when mixed with an acid, therefore requiring special precautions during use. Consequently, the use of cyanide complexing agents present health, safety and regulatory issues.

Examples of suitable sulfur containing complexing agents include, but are not limited to, thiourea and derivatives thereof, thiouronium salts, thiocarboxylic acids, and so forth. A significant advantage of employing a thiourea complexing agent is its high level of compatibility/stability when dissolved in an acidic solution.

More specific examples of suitable thiourea compounds include, for example, N-methylthiourea, N,N'-dimethylthiourea, N,N,N',N'-tetramethylthiourea, N-ethylthiourea, N,N'-diethylthiourea, N,N,N',N'-tetraethylthiourea, N-phenylthiourea, N,N'-diphenylthiourea, N-phenyl-N-methylthiourea, N-phenyl, N'-methylthiourea, N,N'-dibutylthiourea, N-benzylthiourea, N-allylthiourea or N,N'-dicyclohexylthiourea.

Some thiouronium salts are described in U.S. Pat. No. 5,560,814 incorporated by reference herein in its entirety. Such salts may also be employed in combination with thiourea, for example.

Examples of acids suitable for use during the electropolishing step include, but are not limited to, phosphoric, hydrochloric, hydrofluoric, tetrafluoroboric (for titanium, tungsten and other electropositive transition metals), other hydrohalides, and so forth. Sulfuric acid is beneficial because it promotes uniformity and etching and thus is more useful for cleaning steps.

Acids are useful for electrolytic steps involving active transition metals which readily form oxides. Acids reduce the stability of the surface oxides, allowing electrolytic descaling and electropolishing. Advantageously, a halide acid or salt thereof may be employed in the electrolytic bath as well. Examples of such acids or salts thereof include, but are not limited to, the metal halides including the alkali metal halides, alkaline earth halides, transition metal halides, hydrogen halides which when in aqueous solutions are referred to as the hydrohalic acids, and so forth. Specific examples include, but are not limited to, hydrogen chloride (HCl) (hydrochlorous acid in water), sodium chloride (NaCl), sodium fluoride (NaF), calcium chloride ($CaCl_2$), potassium chloride (KCl), magnesium chloride ($MgCl_2$), ferric chloride ($FeCl_3$), and so forth.

The conductivity and viscosity of the solution may be altered by varying the cation employed in combination with the halide such as chloride. The addition of halides has been found to increase the uniformity of the polishing film or balance its properties to provide improved surface finish (smoothness). Halides can act as both charge carriers and complexing agents, and depending on the halide employed, can effectively complex a wide variety of metals. Chlorides, for example, have been found to effectively complex a wide variety of metals while fluorides have been found to effectively complex more electropositive metals such as titanium or tungsten. Bromides and iodides have been found to effectively complex noble metals such as gold or platinum. Chlorides are known pitting agents, but may be balanced carefully with the other solution constituents to prevent these localized corrosion reactions.

During the electrolytic steps, either descaling (cleaning) or electropolishing, the stents are placed in an electrolytic bath and connected to a power supply. In one embodiment, voltage is supplied by a Kepco 5 amp bipolar power supply in constant voltage mode. The power supply is controlled by a Fluke model 39A waveform generator. The electrical connection of the part can be accomplished in a variety of ways, depending on the configuration of the bath and the fixture. In one embodiment, the part is firmly grasped with reverse action, stainless steel tweezers (Techni-Tool, Model 5AX-SA, Part Number 758TW605) and immersed in the bath.

Other contact materials which may be more desirable for used herein include those that are inactive or unreactive to the waveform and chemical composition of the bath, but efficiently delivery voltage to the part. Examples include, but are not limited to, titanium, and its alloys, or thin passive coatings on conductive material that can deliver current through physical contact with the coating, and is otherwise inert to the solution in areas where no physical contact is made with the workpiece or other fixturing components.

Counter electrodes, composed of Pt—Nb, stainless steel mesh or graphite, are typically resident to the electrolytic bath. The counter electrodes are connected to the power supply to complete the circuit. Thus current travels from the power supply, to the fixturing, to the stent, to the electrolytic bath, to the counter electrode and back to the power supply.

Either voltage control or current control can be used to maintain the desired waveform. Preferably, the power supply uses voltage control wherein reactions are sensitive to small changes in voltage. It has been observed that current control results in greater variation of the electropolishing film. Suitably, the positive voltage may be about +3.5 to about 4.2 Volts SCE (versus a saturated calomel electrode). The negative voltage may be about −0.6 to about −0.8 Volts SCE. The rest or delay pulse in between the anodic and cathodic pulses may be biased to help balance the system for optimizing the polishing film (i.e. smoothness of the part). It has been found that small biases on the rest or delay pulse may be applied in the range of −300 mVsce to +300 mVsce. The multiple pulse waveform may be applied during either a descaling step, during a polishing step or during both. The multiple pulse waveform may be a periodic reverse multiple pulse waveform. The part is subjected to a cathodic pulse followed by an anodic pulse. In theory, the cathodic pulse reduces surface oxides to metal.

The anodic pulse then provides energy to solubilize the metal, in the presence of the complexing agent(s). This combination of pulses is then repeated to maintain an active surface. The addition of a rest period (no applied voltage) after the anodic pulse has been found to be beneficial in controlling the film properties for electropolishing by allowing additional diffusion time during which a natural discharge of the part occurs. Such a rest period provides little or no benefit during etching, since etching is generally not diffusion limited. Those skilled in the art will recognize that any number of combinations of repeated pulses bearing the same negative, then positive form will allow successful etching or polishing of the part. Optimization of surface finishes will be achieved by balancing these pulses to generate appropriate polishing film attributes. The presence of multiple negative or multiple positive pulses are included in the described technique.

Suitably, the current is cathodic of about −130 amps per square foot (ASF) to about −390 ASF for a time interval of about 2 milliseconds (ms) to about 1 second and then the current is anodic of about +130 ASF to about +775 ASF for about 4 ms to about 10 sec.

Suitably, the waveform will be anodic-cathodic-anodic or cathodic-anodic-cathodic and so forth, although this pattern may be varied.

The period of each cycle of the waveform may range from about 5 ms to 10 seconds. For cleaning, for example a 500 ms period may be sufficient, while for polishing a 20 ms period may be sufficient. In one embodiment, a −390 ASF 50 ms, +390 ASF 450 ms waveform was found to provide more effective oxide removal and a −130 ASF 4 ms, +390 ASF 6 ms, off 10 ms waveform was more effective for edge rounding and surface smoothing. However, with more complex waveforms the period may increase since there is nothing limiting a completely non-periodic waveform that included pulses of anodic and cathodic current.

Another example of a two pulse waveform for electrocleaning includes an anodic pulse of +550 ASF/450 ms and an anodic pulse of −800 ASF/50 ms.

Obviously, the number of pulses and the magnitudes of the currents may be varied.

The current for each anodic pulse may range from about +200 to about +1000 ASF while the current for each cathodic pulse may range from about −400 ASF to about −1200 ASF, although these ranges are intended for illustrative purposes only, and not as a limitation on the scope of the present invention.

Figure 2:
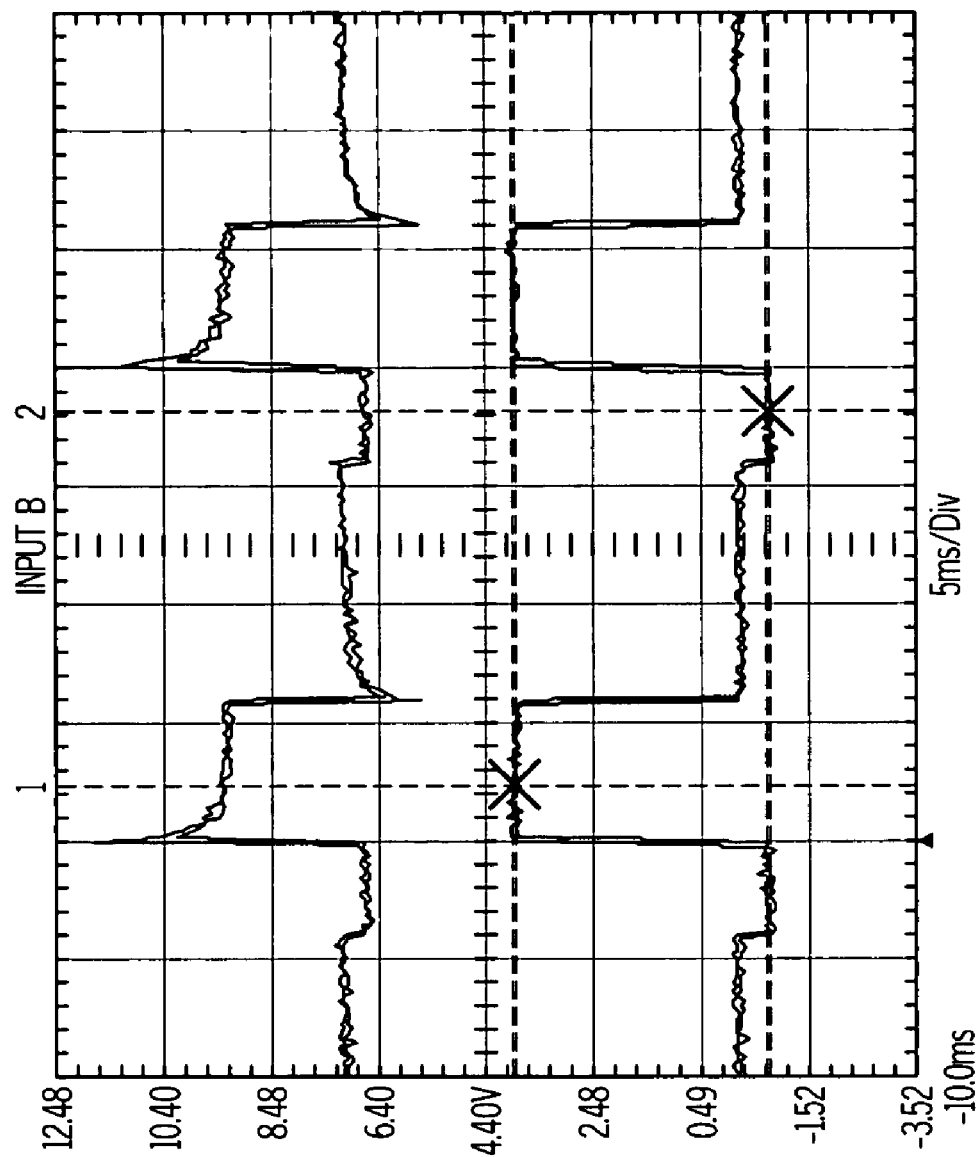
FIG. 2 illustrates a waveform which may be employed in the cleaning and electropolishing processes according to the invention.

FIG. 2 illustrates an example of a three-pulse waveform which may be employed in the cleaning and electropolishing process according to the invention. The figure shows both the input voltage and response current.

As discussed above, a period of rest may be included between each application of voltage or current. Suitable resting periods may be from about 0 to about 100 ms, and more suitably from about 0 to about 10 ms for this application. As noted above, although such resting period(s) are optional, they have been found to be advantageous for use during electropolishing. However, longer periods tend to increase the process time without significant improvement in polishing quality. Additionally, unduly long polishing times can prevent adequate polishing from occurring altogether.

There is a large variety of multiple pulse waveforms that can be employed in the present invention including various combinations of anodic and cathodic pulses followed by periods of rest.

Examples of suitable descaling (cleaning) combinations are found in tables 1–3 below.

TABLE 1

Cleaning (Descaling)

| Compound | Range 1 | Range 2 | Range 3 |
| --- | --- | --- | --- |
| Sodium Chloride (gr NaCl/L) | 1–100 | 30–70 | 50 |
| Potassium Cyanide (gr KCN/L) | 1–100 | 30–70 | 50 |
| Water (cc/L) | Balance 1 L | Balance 1 L | Balance 1 L |

Use of an AC waveform produced satisfactory cleaning at 1300 ASF (amps per square foot). Gas scrubbing of the part was a significant factor in the resulting cleanliness. Cyanide and chloride provide effective complexing of the noble metal(s), while water effectively complexes the active transition metal(s). The salts provide conductivity.

TABLE 2

Cleaning (Descaling)

| Compound | Range 1 | Range 2 | Range 3 |
| --- | --- | --- | --- |
| Water (cc/L) | 0–500 | 40–80 | 50 |
| Thiourea (gr/L) | 5–200 | 50–100 | 75 |
| Hydrochloric Acid (cc HCl/L) | 5–200 | 40–70 | 50 |
| Potassium Chloride (gr KCl/L) | 0–Saturated | 10–30 | 20 |
| Sulfuric Acid | 0–500 | 25–75 | 50 |
| Phosphoric acid | Balance 1 L | Balance 1 L | Balance 1 L |

According to the invention, a periodic reverse current waveform was employed in combination with those compositions shown in table 2, above. In one embodiment, the periodic reverse current waveform included a cathodic 50 ms pulse at −390 ASF (approximately −0.8 Volts SCE) followed by an anodic 450 ms pulse at +390 ASF (approximately +3.8 Volts SCE). Using this method, cleaning can be effectively conducted at room temperature with no agitation, however, the temperature can be elevated and/or agitation can be added. Thiourea and chloride can effectively complex noble metal(s) as well as transition metals, while water, sulfates and phosphates can effectively complex the active transition metal(s).

TABLE 3

Cleaning (Descalng)

| Compound | Range 1 | Range 2 | Range 3 |
|---|---|---|---|
| Water (cc/L) | 0–500 | 10–100 | 23 |
| Sodium Chloride (gr NaCl/L) | 1–100 | 50–100 | 10 |
| Hydrochloric Acid (cc HCl/L) | 20–200 | 35–65 | 140 |
| Sulfuric Acid (cc $H_2SO_4$/L) | 0–200 | 0–100 | 50 |
| Phosphoric acid | Balance 1 L | Balance 1 L | Balance 1 L |

According to the present invention, a periodic reverse, pulse current waveform may be employed in combination with the compositions shown above. In one embodiment, the waveform included +170 ASF for 5 ms followed by −140 ASF for 1 ms. The addition of an acid such as sulfuric, for example, may provide even more uniform current distribution.

After an article or component of an article has been cleaned of adherent oxides, or other non-conducting materials and noble metal films and precipitates, it can be electropolished. This step corresponds to box 6 of FIG. 1.

Examples of suitable electropolishing baths with examples of suitable ranges of ingredients are found in tables 4–7 below.

TABLE 4

Electropolishing

| Compound | Range 1 | Range 2 | Range 3 |
|---|---|---|---|
| Metal (gr/L) | 0–5 | 0–2 | 2 |
| Water (cc/L) | 0–200 | 32–97 | 32 |
| Thiourea (gr/L) | 25–150 | 86–108 | 108 |
| Hydrochloric Acid (cc HCl/L) | 10–50 | 11–32 | 32 |
| Potassium Chloride (gr KCl/L) | 5–50 | 10–21 | 10 |
| Phosphoric acid | Balance 1 L | Balance 1 L | Balance 1 L |

The above compositions exhibit uniform mass removal, good edge rounding, good polishing, required no agitation, were effective at room temperature, and were effective using short cycle times.

In one embodiment, a waveform of −0.8 volts SCE for 4 ms, +3.8 volts SCE for 6m, and a rest period 0 Volts for 10 ms, was employed in combination with the above compositions. Again as noted above, thiourea and chloride for complexation of the noble metal(s) and phosphate and water for complexation of the active transition metal(s) were found to be an effective combination for electropolishing of alloys having both noble and active transition metals. The addition of dissolved metal (e.g. stainless steel), depending on the quantity, may promote bath stability, reducing change in mass removal rate and other parameters as the bath picks up metal from dissolved parts.

TABLE 5

Electropolishing

| Compound | Range 1 | Range 2 | Range 3 |
|---|---|---|---|
| Sodium Chloride | 0–100 | 20–30 | 30 |
| Sodium Sulfate (g Na2SO4/L) | 0–150 | 50–150 | 150 |
| Potassium Cyanide (g KCN/L) | 10–100 | 20–70 | 30 |
| Glycerol (ml/L) | 100–400 | 200–400 | 400 |
| Water | Balance 1 L | Balance 1 L | Balance 1 L |

In one embodiment according to the invention, polishing was conducted using AC at 1300 ASF. Using the above compositions, cyanide and chloride are present for complexation of the noble metal(s) while the sulfate and water are added for complexation of the active transition metal(s). Glycerol may be added to increase the viscosity of the composition. The addition of a halide salt such as NaCl was was found to improve the uniformity of the electropolishing achieved.

TABLE 6

Electropolishing

| Compound | Range 1 | Range 2 | Range 3 |
|---|---|---|---|
| Sodium Chloride (g NaCl/L) | 5–100 | 5–15 | 10 |
| Hydrochloric Acid (cc HCl/L) | 50–200 | 100–150 | 140 |
| Water (ml/L) | 0–50 | 10–30 | 23 |
| Phosphoric Acid | Balance 1 L | Balance 1 L | Balance 1 L |

The above solution may be employed for compositions which have low concentrations of precious metal(s) such as those having about 13% or less. The compositions found in table 6 while effective, may require slightly longer cycle times, for example thirty minutes or more, than some compositions described above. For example, compositions having thiourea appear to provide effective polishing with less time. (approximately 30 minutes polishing time). Again, chloride is added for complexation of the noble metal(s) while water and phosphate are added for complexation of the active transition metal(s). In one embodiment according to the invention, a pulse, periodic reverse polarity current waveform was utilized with +450 ASF for 5 ms and −150 ASF for 1 ms. A rest period is optional.

TABLE 7

Electropolishing

| Compound | Range 1 | Range 2 | Range 3 |
|---|---|---|---|
| Thiourea (g/L) | 25–125 | 50–100 | 60 |
| Sodium Chloride (g/L) | 15–Saturation | 45–Saturation | 60 |
| Water (ml/l) | 200–450 | 250–400 | 300 |
| Phosphoric Acid | Balance 1 L | Balance 1 L | Balance 1 L |

In one embodiment a waveform of −0.8 volts SCE for 4 ms, +3.8 volts SCE for 6 ms, and a rest period of 0 Volts for 10 mS, was added.

Depending on the particular chemistry, waveform and material chosen, the total polishing time may be varied from about 45 seconds to about 60 minutes. Times shorter than this tend to produce inferior edge rounding and surface smoothing, while longer times tend to decrease the efficiency of the production process without providing any further siginificant benefit. Depending on the geometry of the part, it may be advantageous to change the contact point during the polishing, either by fixturing or by breaking the polishing into multiple steps.

The descaling and electropolishing steps may be followed by a surface passivation step. Such surface passivation for stainless steel may be accomplished by using a strong acid such as nitric ($HNO_3$) acid, citric acid or proprietary mixtures. This step is represented by the seventh box in FIG. 1.

A rinsing step (eighth box in FIG. 1) may follow the passivation step followed by drying of the stents (ninth box in FIG. 1). Furthermore, a rinsing step may optionally accompany each step of the process to remove any chemicals used in the previous process prior to submersion in the next bath. This prevents cross-contamination of the compositions employed in each step of the process. This is especially important if the cyanide chemistry is utilized. This risk is minimized if the two solutions are chemically similar or compatible.

The process of the present invention offers several advantages over previously employed processes. For one, the process may be simplified because fewer steps may be required to achieve similar or superior results in polishing or cleaning. No agitation is required and the process is effective at room temperature. The process according to the present invention employs chemicals with relatively low toxicity which are therefore less hazardous for use than cyanide based compositions, for example. The process according to the present invention is also effective for descaling and electropolishing alloys which are untreatable by previously available processes.

Figure 3:
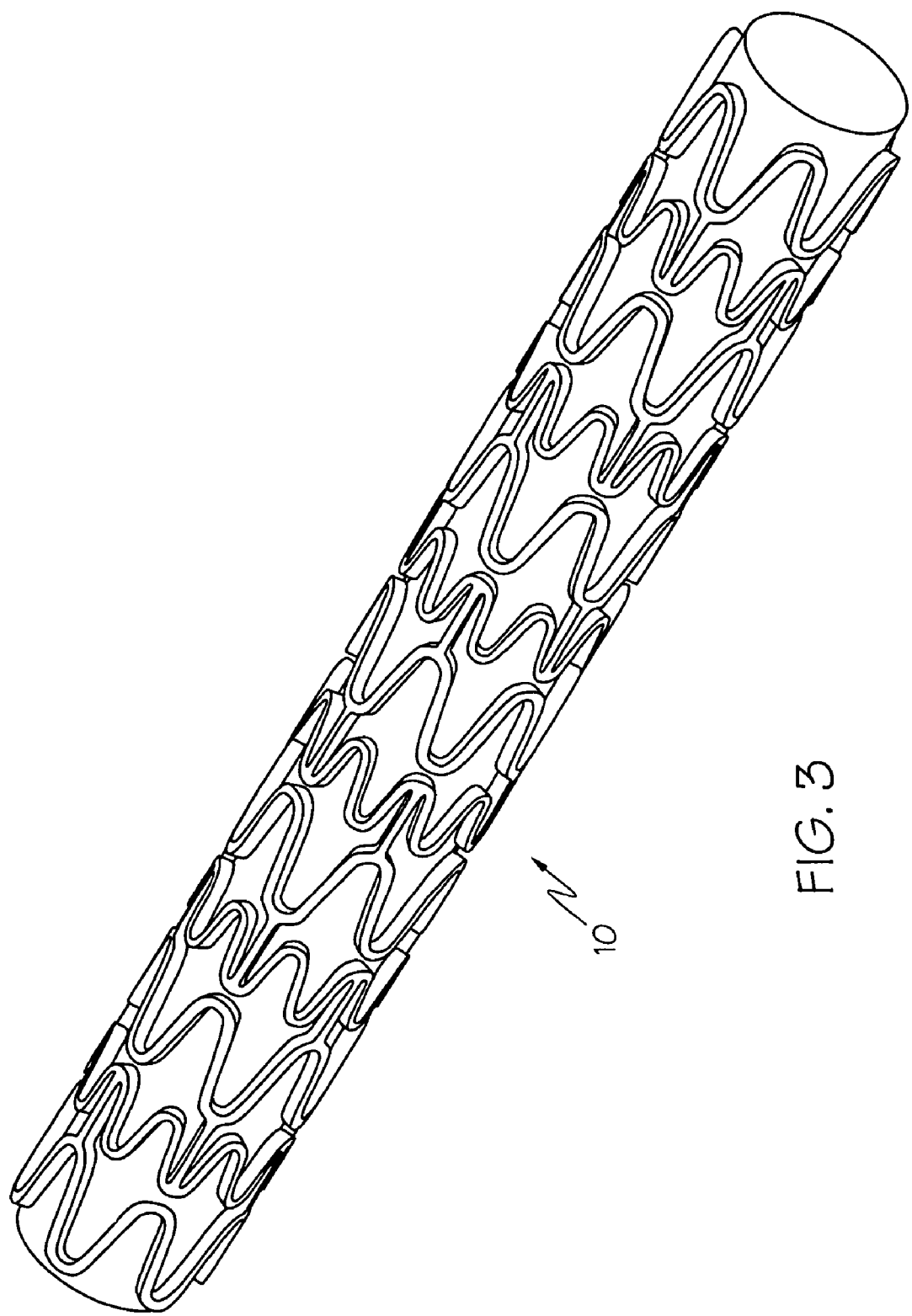
FIG. 3 is a perspective view of a stent which may be formed of an alloy including at least one noble metal and at least one non-noble metal which may be manufactured according to the novel process described herein.

FIG. 3 illustrates one representative embodiment of a stent 10 which may be formed using an alloy which includes at least one noble metal and at least one active transition metal and which may be manufactured according to the present invention. It is recognized that the alloy and the process of manufacturing described herein can be used to form any stent structure. Stents formed of the described platinum-stainless steel alloy are described in commonly assigned copending U.S. patent application Ser. No. 10/112, 391 filed Mar. 28, 2002.

Stents formed according to the present invention have a bright, shiny, smooth surface appearance with good edge (corner) rounding, good surface finish, and relatively uniform mass removal along the length of the part and between strut width and wall thickness. Furthermore, this finish can be achieved with a total mass removal of about 30% to 40% or less. Clearly, lower mass removal reduces the need for reclamation of noble metals. Lower mass removal also may be associated with decreased dimensional variation.

Figure 4:
FIG. 4 is a scanning electron micrograph of a descaled stent prior to polishing.
Figure 5:
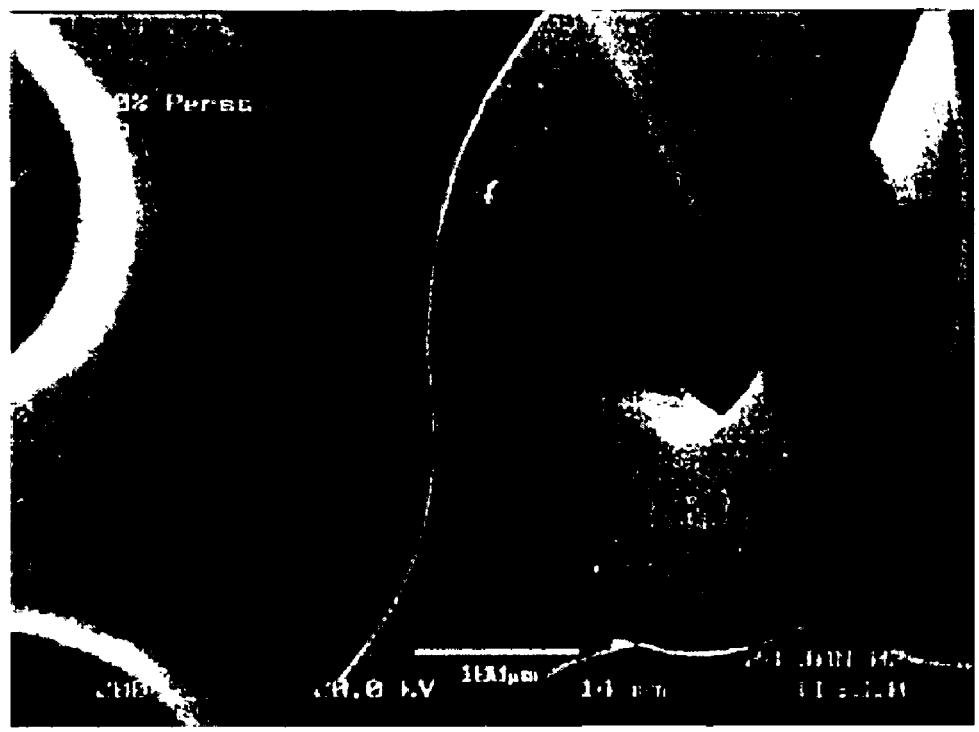
FIG. 5 is a scanning electron micrograph of the descaled stent after polishing.

FIGS. 4 and 5 are scanning electron micrographs of a descaled stent prior to polishing and after polishing according to the invention.

The present invention may find utility for use in cleaning or polishing any article or component of an article formed from an alloy such as those described herein having both noble and active transition metals. The present invention finds particular utility for polishing or cleaning of medical devices such as stents, for example.

The above disclosure is intended to be illustrative and not exhaustive. The description will suggest many variations and alternatives to those of ordinary skill in the art. All of these alternatives and variations are intended to be included within the scope of the attached claims. Those familiar with the art may recognize other equivalents to the specific embodiments described herein which equivalents are also intended to be encompassed by the claims attached hereto.

The invention claimed is:

1. A method of cleaning or electropolishing a stent formed from an alloy comprising at least one noble metal and at least one non-noble metal, the method comprising the steps of:

a) providing a tabular member formed from on alloy comprising at least one noble metal and at least one non-noble metal, said non-noble metal selected from the group consisting of stainless steel, cobalt-chromium alloys, and nickel-titanium alloys;

b) laser cutting a stent pattern in said tubular member to form a stent;

c) electropolishing said stein in an aqueous acidic mixture comprising at least one chelating or complexing agent, said chelating agent comprising at least one sulfur atom and at least one halide in the form of a salt or an acid; and d) subjecting said acidic mixture to a multiple pulse waveform.

2. The method of claim 1 further comprising the step of soaking said stent in an acidic mixture of fluoroboric and nitric acids.

3. The method of claim 1 further comprising the step of etching said stent in an electrolytic acidic bath comprising at least one chelating or complexing agent having at least one sulfur ion before said electropolishing step.

4. The method of claim 1 wherein said multiple pulse waveform is a periodic reverse multiple pulse waveform.

5. The method of claim 1 wherein said chelating agent is selected from the group consisting of thiourea, derivatives of thiourea, thiouronium salts, thiocarboxylic acids or salts thereof and mixtures thereof.

6. The method of claim 5 wherein said chelating agent is selected from the group consisting of thiouronium salts having the general formula:

where $R_1$ to $R_4$ are each hydrogen, $C_1$–$C_8$-alkyl, which may be carboxyl-, $C_1$–$C_4$-alkoxycarbonyl- or cyano-substituted, $C_2$–$C_{12}$-alkenyl, $C_2$–$C_{12}$-alkinyl alkinyl, $C_5$–$C_8$ cycloalkyl, $C_7$–$C_{12}$ phenylalicyl or phenyl which may be substituted by one or two substituents selected from the group consisting of $C_1$–$C_4$ alkyl, $C_1$–$C_4$ alkoxy, halogen, hydroxyl, phenyl and $C_1$–$C_4$ alkoxycarbonyl;

Y is a chemical bond or linear or branched alkylene, alkenylene or alkinylene having in each case up to 20 carbon atoms;

A is hydrogen or a group of the formula —COH, —$COR_5$, —COOH, —$COOR_5$, —$CONR_6R_7$, —$COCH_2COOR_5$, —OCOH, —$OCOR_5$, —$NR_6COR_5$, —$OR_5$, —$SO_2R_5$, —$SO_2OH$, —$SO_2OR_5$, —$PO(OH)_2$, —$PO(OH)(OR_5)$, —PO$(OR_5)_2$, OPO$(OH)_2$, —OPO(OH)($OR_5$) or —OPO$(OR_5)_2$, where $R_5$ is $C_1$–$C_{12}$ alkyl, $C_2$–$C_{12}$ alkenyl, $C_2$–$C_{12}$ alkinyl, $C_5$–$C_8$ cycloalkyl, $C_7$–$C_{12}$ phenylalkyl or phenyl which may be substituted by one or two substituents selected from the group consisting of $C_1$–$C_4$ alkyl, halogen, hydroxyl, phenyl and $C_1$–$C_4$ alkoxycarbonyl, and $R_6$ and $R_7$ are each hydrogen or $C_1$–$C_4$ alkyl;

n is from 1 to 4; and

X is an n-valent inorganic or organic anion that promotes solubility in water.

7. The method of claim 5 wherein said chelating agent is selected from the group consisting of N-metyhbiourea, N,N'-dimethylthiourea, N,N,N',N'-tetramethylthiourea, N-ethylthiourea, N,N'-diethylthiourea, N,N,N',N'-tetraethylthiourea, N-phenylthiourea, N,N'-diphenylthiourea, N-phenyl-N-methylthiourea, N-phenyl-N'-methylthiourea, N,N'-dibutylthiourea, N-benzylthiourea, N-allylthiourea, N,N'-dicyclohexylthiourea and mixtures thereof.

8. The meted of claim 1 wherein said at least one noble metal is selected from the group consisting of gold, silver, platinum, iridium, rhodium, palladium, osmium, and ruthenium.

9. The method of claim 1 wherein said at least one noble metal is a platinum group metal selected from the group consisting of platinum, iridium, rhodium, palladium, osmium and ruthenium.

10. The method of claim 1 wherein said stout is formed from an alloy which is a platinum enriched stainless steel alloy.

11. The method of claim 10 wherein said stent is formed from a platinum-enriched stainless steel alloy comprising platinum, chromium, nickel and iron.

* * * * *